United States Patent
Shah

(10) Patent No.: US 10,582,949 B2
(45) Date of Patent: Mar. 10, 2020

(54) SHEATH ASSEMBLY AND MULTIHOLE CATHETER FOR DIFFERENT FIELDS OF ENDOSCOPIC SURGERY INVOLVING SUCTION, IRRIGATION AND MATERIAL REMOVAL

(71) Applicant: Kaushikkumar Vallabhadas Shah, Surat (IN)

(72) Inventor: Kaushikkumar Vallabhadas Shah, Surat (IN)

( * ) Notice: Subject to any disclaimer, the term of this patent is extended or adjusted under 35 U.S.C. 154(b) by 377 days.

(21) Appl. No.: 15/325,878

(22) PCT Filed: Dec. 19, 2014

(86) PCT No.: PCT/IN2014/000785
§ 371 (c)(1),
(2) Date: Jan. 12, 2017

(87) PCT Pub. No.: WO2016/051421
PCT Pub. Date: Apr. 7, 2016

(65) Prior Publication Data
US 2018/0289394 A1    Oct. 11, 2018

(30) Foreign Application Priority Data
Sep. 30, 2014   (IN) .......................... 3119/MUM/2014

(51) Int. Cl.
*A61B 17/34*     (2006.01)
*A61B 1/00*      (2006.01)
(Continued)

(52) U.S. Cl.
CPC ...... *A61B 17/3423* (2013.01); *A61B 1/00135* (2013.01); *A61B 1/00142* (2013.01);
(Continued)

(58) Field of Classification Search
CPC ............ A61B 17/3423; A61B 1/00131; A61B 1/00142; A61B 1/00154; A61B 1/015;
(Continued)

(56) References Cited

U.S. PATENT DOCUMENTS 4,935,006 A * 6/1990 Hasson ............... A61M 1/0084
604/268
4,955,895 A * 9/1990 Sugiyama ........... A61M 25/104
604/103.1

(Continued)

OTHER PUBLICATIONS

International Search Report for related application No. PCT/IN14/000785 dated Oct. 16, 2015.

*Primary Examiner* — Laura A Bouchelle
*Assistant Examiner* — Mark A Igel
(74) *Attorney, Agent, or Firm* — D'Ambrosio & Menon, PLLC; Usha Menon

(57) ABSTRACT

A sheath assembly for different fields of endoscopic surgery involving suction, irrigation and material removal comprising a tubular sheath including a sheath cannula having an inner open end for introducing into body region requiring surgery and a suction unit with controllable suction provision operatively connected to the outer other open end of the tubular sheath comprising a reservoir. The reservoir includes a reservoir inlet connected in line with the outer other open end of the tubular sheath, a reservoir outlet connected to a suction machine and perpendicularly disposed with respect to the reservoir inlet, a releasably attachable sealing assembly to allow passage of operating endoscope through the reservoir and make assembly of the reservoir and the operating endoscope water and air tight for functioning of the suction unit; and a suction control opening disposed in operative cooperation with said reservoir outlet to provide alternative suction zone in the sheath assembly.

11 Claims, 4 Drawing Sheets

Figure 1:

(51) Int. Cl.
    *A61B 1/015*    (2006.01)
    *A61B 1/018*    (2006.01)
    *A61B 1/313*    (2006.01)
    *A61B 17/32*    (2006.01)
    *A61M 1/00*     (2006.01)
    *A61M 29/00*    (2006.01)
    *A61M 39/20*    (2006.01)
    *A61M 25/00*    (2006.01)
    *A61M 25/06*    (2006.01)

(52) U.S. Cl.
    CPC .......... *A61B 1/00154* (2013.01); *A61B 1/015* (2013.01); *A61B 1/018* (2013.01); *A61B 1/313* (2013.01); *A61B 17/320016* (2013.01); *A61B 17/3498* (2013.01); *A61M 1/0031* (2013.01); *A61M 1/0058* (2013.01); *A61M 29/00* (2013.01); *A61M 39/20* (2013.01); *A61B 2017/320044* (2013.01); *A61B 2217/005* (2013.01); *A61B 2217/007* (2013.01); *A61M 25/007* (2013.01); *A61M 25/0662* (2013.01); *A61M 2210/1082* (2013.01)

(58) Field of Classification Search
    CPC ....... A61B 1/018; A61B 1/0031; A61B 1/313; A61B 1/0058; A61B 2217/005; A61B 2217/007; A61M 2025/0004; A61M 1/0058; A61M 39/20
    See application file for complete search history.

(56) References Cited

U.S. PATENT DOCUMENTS

| | | | | |
|---|---|---|---|---|
| 5,047,045 A * | 9/1991 | Arney | ................ | A61M 25/104 604/103.1 |
| 5,207,648 A * | 5/1993 | Gross | ................ | A61M 25/0014 604/164.09 |
| 5,250,059 A * | 10/1993 | Andreas | ......... | A61B 17/320783 604/22 |
| 5,458,574 A * | 10/1995 | Machold | ............ | A61M 25/1011 604/101.03 |
| 5,575,756 A * | 11/1996 | Karasawa | .......... | A61B 1/00068 600/121 |
| 5,637,075 A | 6/1997 | Kikiwada | | |
| 2001/0016751 A1* | 8/2001 | Trerotola | ............. | A61B 17/221 606/159 |
| 2002/0072651 A1* | 6/2002 | Vilos | ......... | A61B 1/12 600/105 |
| 2003/0097133 A1* | 5/2003 | Green | ................. | A61B 17/1617 606/80 |
| 2003/0130565 A1* | 7/2003 | Muller | ............... | A61B 1/00071 600/156 |
| 2003/0144594 A1* | 7/2003 | Gellman | ............. | A61B 1/015 600/466 |
| 2005/0020966 A1* | 1/2005 | Soring | ........... | A61B 17/320068 604/22 |
| 2005/0059931 A1* | 3/2005 | Garrison | ............... | A61M 25/10 604/101.04 |
| 2005/0234298 A1* | 10/2005 | Kucklick | ........... | A61B 1/00135 600/156 |
| 2006/0129091 A1* | 6/2006 | Bonnette | ................ | A61B 17/22 604/93.01 |
| 2006/0229645 A1* | 10/2006 | Bonnette | .......... | A61B 17/00234 606/159 |
| 2006/0266423 A1* | 11/2006 | Akiba | .................. | A61M 3/0258 137/565.01 |
| 2006/0276692 A1* | 12/2006 | Kucklick | .......... | A61B 1/00135 600/175 |
| 2007/0118072 A1* | 5/2007 | Nash | ...................... | A61B 17/22 604/35 |
| 2007/0184717 A1* | 8/2007 | Hamazaki | .......... | A61B 1/00137 439/607.01 |
| 2008/0208004 A1* | 8/2008 | Okada | ................ | A61B 1/00068 600/156 |
| 2009/0069829 A1* | 3/2009 | Shturman | ....... | A61B 17/320725 606/159 |
| 2009/0275893 A1* | 11/2009 | DiBiasio | ............ | A61B 17/3421 604/119 |
| 2009/0312696 A1* | 12/2009 | Copa | .................... | A61M 25/007 604/43 |
| 2012/0215067 A1* | 8/2012 | Kucklick | ........... | A61B 1/00135 600/114 |

\* cited by examiner

SHEATH ASSEMBLY AND MULTIHOLE CATHETER FOR DIFFERENT FIELDS OF ENDOSCOPIC SURGERY INVOLVING SUCTION, IRRIGATION AND MATERIAL REMOVAL

FIELD OF THE INVENTION

The present invention relates to a sheath assembly for different fields of endoscopic surgery involving suction, irrigation and material removal. More specifically, the present invention relates to a sheath assembly for different fields of endoscopic surgery which would on one hand enable reducing the size of a keyhole for endoscopic surgery. The reduced keyhole size makes the endoscopic surgery minimally invasive by reducing damage to surrounding organ, reduced bleeding, faster recovery and early discharge. While on the other hand providing the advantages of big hole surgery. Advantageously, the sheath assembly for different fields of endoscopic surgery of the invention is directed to make vision clear making the procedure faster, arrest stone from flying away from visual field and enable complete clearance of stone easier and faster. The sheath assembly of the invention would enable using variety of sheath sizes of different length and width of working sheath and thus facilitate applying to neonates as well as morbidly obese patients. Importantly also, the sheath assembly is directed to achieve endoscopic surgery such as percutaneous renal surgery with even about 3.0 mm inner diameter tubular sheath for large varieties of stones which previously essentially required about 5 to 8 mm size sheaths to achieve like results. Thus, the sheath assembly of the invention is directed to add comfort and extra safety both for the patient as well as the surgeons.

BACKGROUND ART

Endoscopic surgery is very popular surgery procedure due to its less complex and faster recovery procedure. Endoscopic surgery is always preferred than conventional surgery. The, endoscopic surgery does have importance such as percutaneous renal surgery which has a big role to play in upper tract diseases and urolithiasis. As is well known in case of percutaneous renal surgery, a ureteric catheter is placed retrograde in the pelvis. Under image guidance a puncture is made in pelvicalyceal system (PCS). A guide wire is then placed in PCS via puncture needle. Tract from skin to PCS is dilated on a guide wire by dilators varying from 5 mm (15 F, 3 F=1 mm) to 10 mm (30 F) diameter. After dilatation, a renal sheath in form of hollow tube of uniform diameter is placed extending from skin to PCS.

Currently in use renal sheath is a hollow tube of uniform diameter, made of plastic or metal. The inner end can be straight or obliquely cut. Outer end is straight. Both ends are open to allow free passage of fluid and endoscope.

Such renal sheath allows repeated entry of operating endoscope from outside body to PCS. Operating endoscope may have a channel for normal saline irrigation, to pass different forceps, suction cannula and energy probes. Renal sheath allows fluid to come out by the side of endoscope.

It is important to take note that when sheath size is small, the provision of suction cannula in the endoscope is not present. Here suction cannula is passed via instrument channel of the operating endoscope to suck out fluid and fragments. Hence size of suction cannula is small leading to aspiration of only small fragments. As the outer end of the sheath is open to air, the sheath cannot be used for suction.

If the sheath size is only marginally bigger than the diameter of the endoscope, all fluid cannot come out easily and intra renal pressure can rise and it may lead to different medical complications. In this scenario, stone fragments may not come out easily especially in dilated flabby pelvicalyceal system.

In order to use suction cannula via endoscope, diameter of endoscope has to be bigger. To use bigger endoscope, sheath size has to be bigger leading to large size of opening in the body. To put large sheath, the surgeon need to dilate the tract with associated risk of losing the tract, bleeding and clots in pelvicalyceal system. Large hole in the body leads to more chances of bleeding, leakage of fluid/urine and more chances of injury to surrounding organs. It leads to use of nephrostomy, stents and catheters at the end of procedure. It increases the postoperative pain and delays recovery. It leads to prolonged hospital stay and increased medical cost. It is thus not possible to use smaller keyhole for percutaneous renal surgery and other surgery.

In scenario where sheath size is small, there is thus no provision of suction at all, compromising the fluid & pressure dynamics of PCS with its own problems.

OBJECTS OF THE INVENTION

It is thus the main object of the present invention is to provide for a sheath assembly for endoscopic surgery such as percutaneous renal surgery which would enable reducing keyhole size to do the endoscopic surgery to make the endoscopic surgery minimally invasive, and ensure faster recovery and early discharge.

Another object of the present invention is directed to a sheath assembly for different fields of endoscopic surgery such as percutaneous renal surgery which would make vision clear making the procedure faster, arrest stone from flying away from visual field and enable complete clearance of stone easier and faster.

Yet another object of the present invention is directed to a sheath assembly for different fields of endoscopic surgery such as percutaneous renal surgery which would enable using variety of sheath sizes of different length and width of working sheath and thus facilitate applying to neonates as well as morbidly obese patients.

A further object of the present invention is directed to the development of a sheath assembly which would facilitate carrying out endoscopic surgery such as percutaneous renal surgery with even about 3.0 mm inner diameter tubular sheath for large varieties of stones which previously essentially required about 5 to 8 mm size sheaths to achieve like results.

Another object of the present invention is directed to a sheath assembly which would add desired comfort and extra safety both for the patient as well as the surgeons in carrying out endoscopic surgery such as percutaneous renal surgery.

A further object of the present invention is to provide for advancement in sheath assembly which would serve to reduce the size of keyhole to do endoscopic surgery so that we can avoid all above mentioned complication related to tract size making it minimally invasive surgery and yet at the same time achieve advantages of big hole surgery.

Another object of the present invention is directed to provide for sheath assembly for different fields of endoscopic surgery such as percutaneous renal surgery which would be a close system and there would be minimal chance of spillage of fluid in operative field and all the material drained out can be completely collected in suction bottle with no extra effort.

Yet further object of the present invention is to advancements in working sheath which would enable its use as suction cannula so that larger fragments can be sucked out, fluid can be sucked out leading to controlled intra renal pressure during surgery.

Another object is to provide for a sheath assembly whereby suction during laser lithotripsy and pneumatic lithotripsy would help to remove dust and small fragments and make vision clear making the procedure faster and does not allow stone to fly away from the visual field and achieve easier and faster complete clearance of stone.

A further object of the present invention is directed to sheath assembly which would involve smaller diameter sheath and also does not need to dilate the tract thereby leading to minimal damage to surrounding organ and practically no bleeding, faster recovery and early discharge.

Another object of the present invention is directed to the development of an ureteric catheter which would benefit surgeons in effectively carrying out endoscopic surgery such as percutaneous renal surgery such as the removal of stones from the renal pelvic with more precision and accuracy and at the same time causing lesser pain and discomfort to the patient.

A further object of the present invention is directed to a kit suitable for carrying our endoscopic surgery involving suction, irrigation and material removal involving a sheath assembly and a ureteric catheter.

Yet further object of the present invention is directed to a method for carrying out endoscopic surgery involving suction, irrigation and material removal involving the sheath assembly and/or the ureteric catheter in accordance with the present invention.

SUMMARY OF THE INVENTION

Thus according to the basic aspect of the present invention there is provided a sheath assembly for different fields of endoscopic surgery involving suction, irrigation and material removal comprising:

a tubular sheath having an inner open end adapted for introducing into the body region requiring surgery and an outer other open end;

a suction unit with controllable suction provision operatively connected to said outer other open end of said tubular sheath enabling selective suction effect inside the tubular sheath in said body region requiring surgery and transmitting of suction pressure to said body region requiring surgery such that during operative process when there is no suction effect inside the tubular sheath only fluid and particles can release by overflowing from the body region requiring surgery for continuous release from said suction unit and when suction pressure is transmitted to said body region requiring surgery via sheath operative fragments can be easily suctioned out from said body region requiring surgery.

According to a preferred aspect of the present invention there is provided a sheath assembly for different fields of endoscopic surgery involving suction, irrigation and material removal comprising:

a tubular sheath having an inner open end adapted for introducing into the body region requiring surgery and an outer externally accessible other rear open end;

a suction unit with controllable suction provision operatively and releasably connectable to said outer externally accessible other open end of said tubular sheath enabling selective suction effect inside the tubular sheath in said body region requiring surgery and transmitting of suction pressure to said body region requiring surgery such that during operative process when there is no suction effect inside the tubular sheath only fluid and particles can release by overflowing from the body region requiring surgery for continuous release from said suction unit and when suction pressure is transmitted to said body region requiring surgery via sheath operative fragments can be easily suctioned out from said body region requiring surgery.

In accordance with another aspect of the present invention in the sheath assembly as above said suction unit comprises a reservoir which can be of any suitable shape with a reservoir inlet which is operatively in line with and releasably connected to said outer other open end of said tubular sheath and a reservoir outlet facing downwards to facilitate the gravitational release of contents entering the reservoir through said reservoir outlet, said reservoir outlet being connected to a suction machine with a suction controlling opening in the reservoir exactly opposite to the said reservoir outlet and an outlet tube connecting said reservoir outlet to said suction machine.

The said suction controlling opening can be disposed at any other suitable place other than exactly opposite to the said reservoir outlet.

According to a further aspect of the present invention in the sheath assembly as above said suction unit comprises a sealing assembly releasably attachable to said suction unit to make the assembly water and air tight for desired functioning of the suction unit and also allow passage of operating endoscope/instruments for surgery there through to said body region requiring surgery.

According to yet another aspect of the present invention in the sheath assembly as above said sealing assembly comprises a sealing flap adjacent the front end disposed in line with the inlet opening of said reservoir which is in turn in line with the tubular sheath passage and a sealing cap on the outside.

According to yet further aspect of the present invention in the sheath assembly as disclosed above after assembling of the tubular sheath for percutaneous surgery said suction controlling opening enables switching on and off the suction effect from inside the sheath such that when said suction controlling opening is open to air, there is no suction effect inside the sheath and only water and dust can overflow from the said body region requiring surgery but there is continuous suction from reservoir and when the said suction controlling opening is closed, suction pressure is transmitted to said body region requiring surgery vis sheath and operative fragments sucked out easily through said reservoir.

According to yet further aspect of the present invention in the sheath assembly as above said sealing assembly can be releasably connected to facilitate the operative process involving any releasable connection means including thread and screw mechanism with sealing ring and said sealing assembly is releasably connected to said suction unit involving any releasable connection means including thread and screw mechanism with sealing ring.

According to a further aspect of the present invention in the sheath assembly as above said suction unit with said reservoir cooperating with said sheath enable selectively involving sheath with reduced dimension favouring minimally invasive surgery and also achieve advantages of big hole surgery.

According to a further aspect of the invention the sheath assembly as discussed above comprises means for controlling intra renal pressure during surgery with clear vision and selective length and width of the said working renal sheath depending upon the patient and purpose of surgery.

According to another aspect of the present invention in the sheath assembly as above the reservoir enables collection of operative fragments in the suction passage preventing its going back to said body region requiring surgery free of involvement of any mechanical valve.

According to yet further aspect of the present invention there is provided a sheath assembly wherein the said sheath and inlet diameter of suction unit is smaller than the outlet diameter whereby everything that is sucked into the reservoir can be suctioned out preferably involving gravity force as well by positioning the said reservoir outlet at the lower end of said reservoir facing downwards and preferably disposed substantially perpendicular to said reservoir inlet.

According to a preferred aspect of the present invention there is provided for a sheath assembly as above which is a renal sheath assembly for percutaneous renal surgery comprising:

said sheath comprising a tubular renal sheath having a front open end adapted for introducing into the pelvicalyceal system and an externally accessible other rear open end;

said suction unit operatively and releasably connectable to said externally accessible other rear open end of said renal sheath enabling selective suction effect inside the renal sheath and transmitting of suction pressure to said pelvicalyceal system such that during operative process when there is no suction effect inside the sheath only water and dust can release by overflowing from the pelvicalyceal system for continuous release from said suction unit and when suction pressure is transmitted to said pelvicalyceal system via sheath operative fragments can be easily suctioned out from said pelvicalyceal system.

According to yet further aspect of the present invention there is provided a sheath assembly as above wherein said sealing flap is a silicon flap valve.

According to yet further aspect of the present invention there is provide for a sheath assembly as above wherein said tubular sheath is adapted to house a dilator cum obturator with one end tapered for a short distance and inside diameter allowing passage of a guide wire.

According to a further aspect of the present invention there is provided for a sheath assembly as above wherein said sheath allows entry of the operating endoscope via sealing cap to silicon flap valve to reservoir to inlet and when the sheath is placed in said body region requiring surgery/said pelvicalyceal system, the operating endoscope can be introduced and taken out including for creating space for suction of big fragments easily without losing tract.

According to yet further aspect of the present invention there is provided for a sheath assembly as above wherein the sheath is obtained of any suitable biocompatible transparent or opaque material including stainless steel and of different diameter and length, said suction unit is obtained of brass but it can be made of stainless steel or any material which can be used in making surgical instrument.

According to another aspect of the present invention there is provided for a sheath assembly as above comprising ureteric catheter with holes at a distance of 1 cm in first 10 cm for retrograde flow of fluid in said pelvicalyceal system and stop passage of fragments going down the ureter.

According to yet further aspect of the present invention there is provided for a sheath assembly as above wherein the reservoir comprise a cylindrical reservoir and at inlet is in form of perpendicular wall such that anything that comes at the end of the sheath falls in the reservoir and has no chance of going back into the sheath.

In accordance with a further aspect of the present invention there is provided for a ureteric catheter suitable for flow of saline/fluids into the renal pelvis during surgery such as required in endoscopic surgery involving suction, irrigation and material removal comprising an open ended tubular catheter along with multiple side openings/holes spaced at least towards the front portion thereof adapted for insertion in the ureter and the renal pelvis region for facilitating controlled flow through the catheter during surgery enabling controlling pressure flow kinetics of renal pelvis during surgery.

According to another aspect the ureteric catheter as above includes said multiple side openings are suitably spaced and disposed such that upon insertion in the ureter and the renal pelvis region the side openings/holes are disposed such that some are in the region of the ureter and some in the renal pelvis to ensure controlled and selective retrograde flow of fluid/contrast/air introduced via the ureteric catheter uniformly and/or selectively towards a direction of renal pelvis to suit the surgery.

According to yet another aspect of the present invention the ureteric catheter as above comprises a terminal open end with markers at equidistance to facilitate catheter insertion and having of uniform diameter to facilitate saline/fluid flow there through.

According to another aspect of the present invention there is provided for a method for carrying out endoscopic surgery involving suction, irrigation and material removal involving the sheath assembly as disclosed above comprising:

(i) assembling the sheath assembly by connecting the tubular sheath to suction unit having said sealing assembly;

(ii) connecting the reservoir outlet to suction machine;

(iii) placing the tubular sheath in said body region requiring surgery/said pelvicalyceal system and passing operating endoscope into said tubular sheath via said sealing cap through silicon flap through reservoir through inlet and placing in said body region requiring surgery/said pelvicalyceal system such that the said endoscope can be taken out and reintroduced without losing tract;

(iv) carrying out the endoscopic surgery involving said sheath assembly maintaining the suction machine on during the process and selectively keeping the suction controlling opening (a) open to air when no suction effect inside the sheath is desired and allowing only fluid and particles to drainout by overflowing from said body region requiring surgery/said pelvicalyceal system which is continuously sucked from the reservoir through said suction and (b) closed to air when the suction pressure is required to be transmitted to said body region requiring surgery/said pelvicalyceal system via tubular sheath and the operative fragments are sucked out easily.

According to another aspect of the present invention there is provided a method for carrying out endoscopic surgery involving suction, irrigation and material removal involving the kit as above comprising:

(i) assembling the sheath assembly by connecting the tubular sheath to suction unit having said sealing assembly;

(ii) connecting the reservoir outlet to suction machine;

(iii) placing the tubular sheath in said body region requiring surgery/said pelvicalyceal system and passing operating endoscope into said tubular sheath via said sealing cap through silicon flap through reservoir through inlet and placing in said body region requiring surgery/said pelvicalyceal system such that the said endoscope can be taken out and reintroduced without losing tract;

(iv) inserting a multiple side hole ureteric catheter in the renal pelvis such that some side holes are in the ureter and some are in the renal pelvis to facilitate retrograde flow of fluids/normal saline from ureter and renal pelvis towards inner end of tubular sheath and controlling pressure flow kinetics of renal pelvis during surgery and/or facilitating discharge of operative fluid and fragments through alternative pathway to outside the body through the sheath and avoiding problems of fragments going down the ureter and blocking of ureter;

(v) carrying out the endoscopic surgery involving said sheath assembly maintaining the suction machine on during the process and selectively keeping the suction controlling opening (a) open to air when no suction effect inside the sheath is desired and allowing only fluid and particles to drain out by overflowing from said body region requiring surgery/said pelvicalyceal system which is continuously sucked from the reservoir through said suction and (b) closed to air when the suction pressure is required to be transmitted to said body region requiring surgery/said pelvicalyceal system via tubular sheath and the operative fragments are sucked out easily.

According to a further aspect of the invention the method as above is carried out involving said multi hole ureteric catheter fluid is allowed to flow into the ureteric catheter from open outer end of ureteric catheter, and the arrangement of multiple holes is involved to ensure free flow of fluid/saline from ureter to renal pelvis in all areas of pelvis where there is hole and towards the inner end of the sheath assembly in the body.

According to yet further aspect of the present invention in the method as above during operation including of percutaneous renal surgery, there is continuous/intermittent flow from nephroscope regulated by stopcock and there is continuous flow of normal saline from multihole ureteric catheter, said multiple holes, some in ureter &some in renal pelvis ensures flow from ureter & renal pelvis towards the inner end of sheath all the time during the operation.

According to another aspect of the invention in the said method as above for giving space in the sheath for big fragments to come out, the endoscope is taken out from the sheath gradually.

According to yet further aspect of the present invention there is provided for said method as above wherein the drained out and/or sucked out fluid and/or fragments are collected in the reservoir and then drained out of the reservoir.

DETAILED DESCRIPTION OF THE INVENTION

Figure 2:
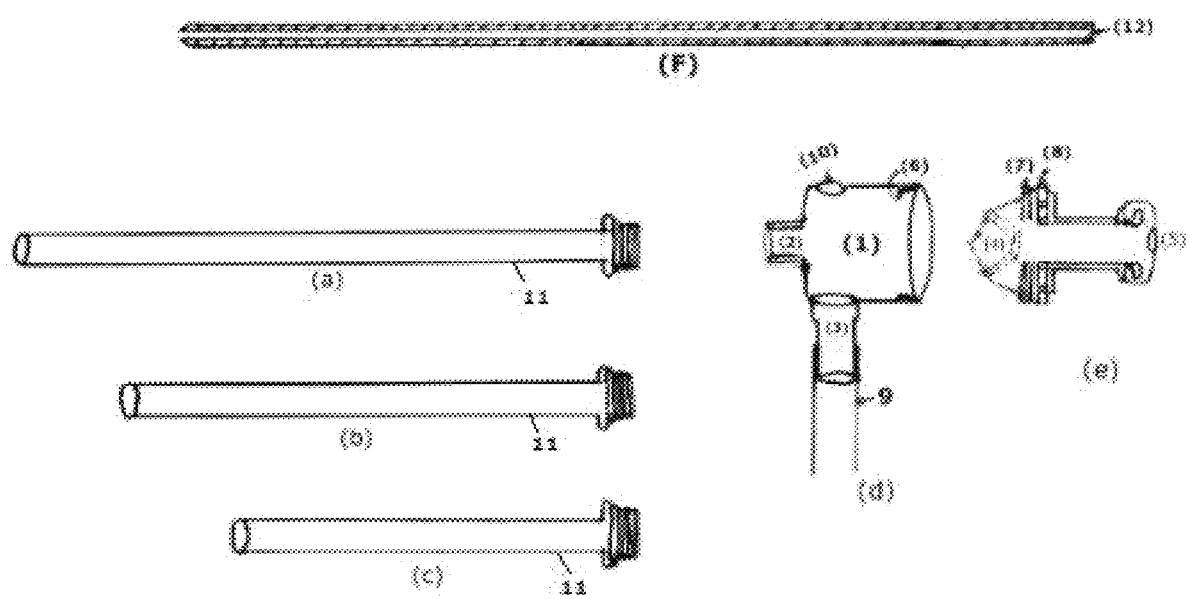

The details of the invention, its objects and advantages are explained hereunder in greater detail in relation to the following non-limiting illustrations as per the following accompanying figures wherein:

FIG. 1: is an illustration of a sheath conventionally used in endoscopic surgery;

FIGS. 2 (*a*), (*b*) and (*c*): are illustrations of tubular sheath part of varying sized and diameter of the sheath assembly for endoscopic surgery in accordance with the present invention;

FIG. 2 (*d*): is an illustration of the suction unit used in the sheath assembly in accordance with the present invention;

FIG. 2 (*e*): is an illustration of the sealing assembly being a reliably connected part of the suction unit shown in FIG. 2 (*d*) above; and FIG. 2 (*f*): is an illustration of dilator cum obturator used in the sheath assembly of the present invention.

Figure 4:
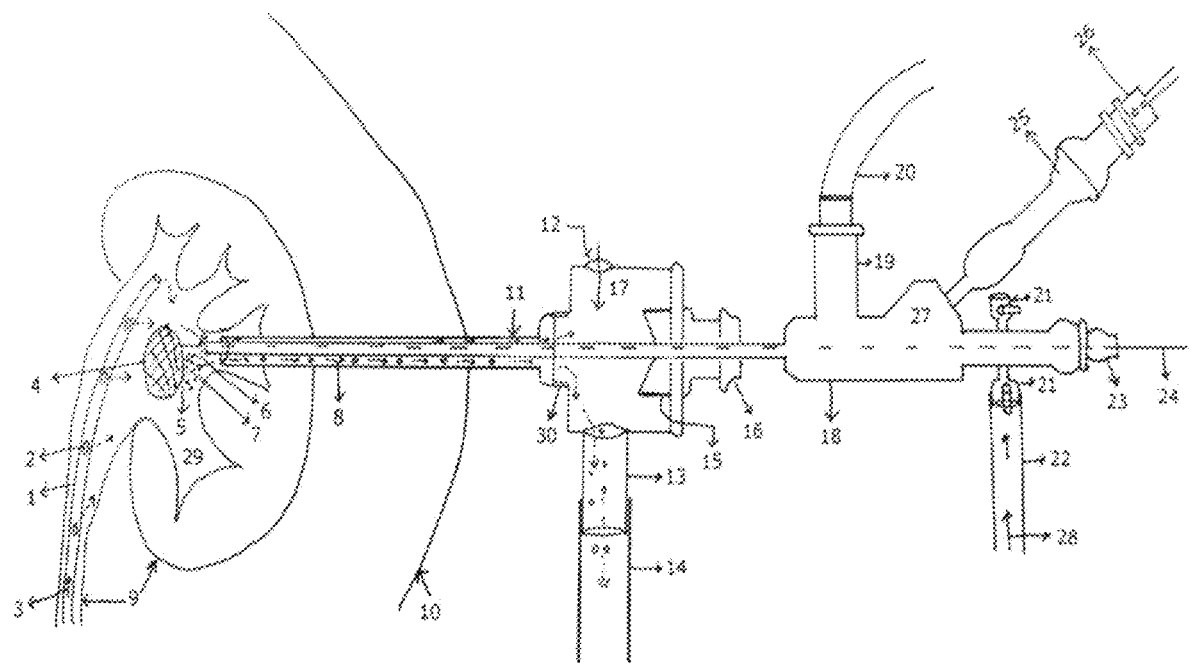

FIG. 3(*a*): is an illustration of an existing renal sheath based operative gadgets and its assembly with respect to the renal sheath involved in the operative procedure;

FIG. 3(*b*): is another illustration of an existing renal sheath based operative gadgets and its assembly with respect to the renal sheath involved in the operative procedure;

FIG. 4: is an illustration of a sheath assembly sheath based operative gadgets and its assembly with respect to the sheath assembly in accordance with the present invention for different fields of endoscopic surgery involving suction, irrigation and material removal involved in the operative procedure.

Figure 5:
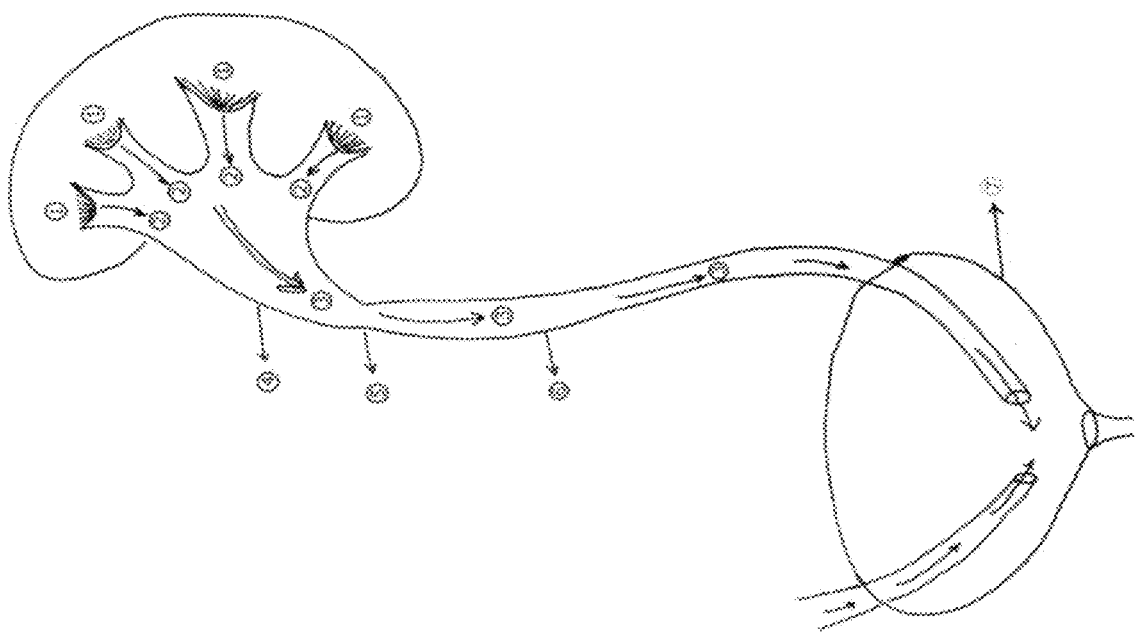
Figure 6:
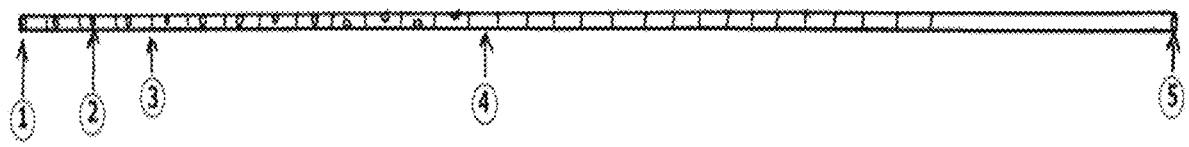

FIG. 5: illustrates the flow of fluid & pressure kinetics in renal pelvis during normal circumstances; and FIG. 6: is an illustration of open ended multiple side holes based ureteric catheter in accordance with another aspect of the present invention;

Reference is first invited to accompanying FIG. 1 which illustrates a conventional renal sheath which is basically a hollow tube of uniform diameter. Usually, the same is made of plastic or metal. The inner end can be straight or obliquely cut while the outer end is straight.

Such a conventional renal sheath is known to be used in percutaneous renal surgery which has a big role to play in upper tract diseases and urolithiasis. Here a ureteric catheter is placed retrograde in the pelvis. Under image guidance a puncture is made in pelvicalyceal system (PCS). A guide wire is placed in PCS via puncture needle. Tract from skin to PCS is dilated on a guide wire by passing serial dilators of gradually increasing size varying from 2 mm (6 F, 3 F=1 mm) to 10 mm (30 F) diameter. This serial dilatation has problems of bleeding from the tract, loss of tract, slippage of the guide wire outside during dilatation and dilatation of the wrong tract. After dilatation, the renal sheath in form of hollow tube of uniform diameter as shown in accompanying FIGS. 1*a* and 1*b* is placed extending from skin to PCS.

As would be apparent from said FIGS. 1*a* and 1*b* the renal sheath is a hollow tube of uniform diameter, made of plastic or metal. The inner end can be straight or obliquely cut. Outer end is straight. Both ends are open to allow free passage of fluid and endoscope.

The renal sheath allows repeated entry of operating endoscope from outside body to PCS. Operating endoscope may have a channel for normal saline irrigation, to pass different forceps, suction cannula and energy probes. Renal sheath allows fluid to come out by the side of endoscope.

Thus when sheath size is small, the provision of suction cannula in the endoscope is not present. Here suction cannula is passed via instrument channel of the operating endoscope to suck out fluid and fragments. Hence size of suction cannula is small leading to aspiration of only small fragments. As the outer end of the sheath is open to air, the sheath cannot be used for suction. If the sheath size is only marginally bigger than the diameter of the endoscope, all fluid cannot come out easily and intra renal pressure can rise and it may lead to different medical complications. In this scenario, stone fragments may not come out easily especially in dilated flabby pelvicalyceal system.

In order to use suction cannula via endoscope, diameter of endoscope has to be bigger. To use bigger endoscope, sheath size has to be bigger leading to large size of opening in the body. To put large sheath, it is important to dilate the tract with associated risk of losing the tract, bleeding and clots in pelvicalyceal system. Large hole in the body leads to more chances of bleeding, leakage of fluid/urine and more chances of injury to surrounding organs. It leads to use of nephrostomy, stents and catheters at the end of procedure. It increases the postoperative pain and delays recovery. It leads to prolonged hospital stay and increased medical cost. Moreover, it is not possible to use smaller keyhole for percutaneous renal surgery and other surgery. In scenario where sheath size is small, there is no provision of suction at all, compromising the fluid & pressure dynamics of PCS with its own problems.

Reference is now invited to accompanying FIGS. 2a, 2b and 2c which illustrate various sizes of sheaths suitable for use as a part of the sheath assembly in accordance with the present invention. As shown in said FIGS. 2a,2b and 2c, the sheath comprises a tubular sheath (11) of uniform diameter of different length & width having an inner end and an outer end and provided with mechanism at the outer end to attach suction unit shown in FIGS. 2 (d) and 2 (e).

As shown in FIG. 2(d), the suction unit basically comprises of reservoir (1) with inlet (2), outlet tube (3), opening in reservoir to control the suction(10) and sealing assembly (FIG. 2e).

The sealing assembly of FIG. 2(e) attaches to reservoir (1). It has sealing silicon flap valve (4) on inner side and sealing cap on outside (5). Its main function is to allow passage of telescope without air or water leak. This makes the sheath assembly water and air tight for suction to work.

FIG. 2 (f) illustrates a dilator cum obturator. It is a hollow tube of suitable diameter to fit inside sheath (FIG. 2a, 2b, 2c). One end is tapered for a short distance of few mm (4 to 8) Inside diameter (11) is enough to allow passage of 0.038 inch guide wire.

The tubular sheath (11) (FIG. 2a, b, c) is attached to suction unit (FIG. 2d-2) by screw and thread with O sealing ring. Suction unit is thus basically made of two parts (FIG. 2d, 2e). It is attached to each other by thread and screw mechanism (6, 7) and O sealing ring (8). Reservoir outlet is connected to suction machine with suction tube (9).

Operating endoscope is passed into sheath (11) (FIG. 2b) via sealing cap (5) to silicon flap valve (4) to reservoir (1) to inlet (2). When sheath is placed inside PCS, it is possible to go in and come out easily without losing tract.

There is a suction controlling opening (10) in the reservoir (FIG. 2d) exactly opposite to outlet tube (3). Silicon suction tube (9) is attached to outlet (3) of reservoir. Other end of suction tube (9) is attached to suction machine. The suction machine is always on during the procedure. When the suction controlling opening (10) is open to air, there is no suction effect inside the sheath but water and dust can come out by overflowing from PCS but there is continuous suction from reservoir. When the suction controlling opening (10) is closed by finger, suction pressure is transmitted to PCS via sheath and fragments come out easily. It is thus possible involving the sheath assembly of the invention which includes a suction unit to take out endoscope from sheath gradually giving a space in the sheath for big fragments to come out. Advantageously, it is possible to actually see the whole path taken by fragment while coming out. Once it has fallen into reservoir (1), there is no chance for fragment to go back into PCS due to design of suction unit.

As distinct from the sheath assembly of the present advancement, as shown in FIG. 1, sheath of prior art is simply a tube open at both ends with no mechanism to attach suction device.

In the present invention, the sheath is a tube, which is much smaller in diameter as compared to conventional sheath and outer end has a mechanism to attach suction unit. It has multiple advantages.

In prior art, if there is suction tube it passes via instrument channel of operative endoscope and whole suction mechanism is in the hands of operating surgeon making it very heavy and cumbersome to use.

In the present invention, suction unit is totally new construction previously not known. It includes a sealing assembly with silicon flap valve (4) used widely to provide sealing effect to reservoir.

The silicon suction tube (9) is widely used silicon tube for various purposes.

The tubular sheath (2a, 2b, 2c) of the sheath assembly of the invention can be preferably made of stainless steel. It can also be made of any material which is biocompatible, can withstand sterilization process, stiff enough and resistant to laser energy. It can be transparent or opaque. It can be of different in diameter and length. The mechanism to attach to suction unit is by screw and thread but it can be in any way which is user friendly and leak proof.

Suction unit as mentioned hereinbefore and illustrated by way of accompanying FIGS. 2(d) and 2(e) has two parts. One part includes reservoir (FIG. 2d) with inlet, opening to control suction power, outlet and mechanism to attach to sealing assembly. Inlet has to be at least equal to or more than the diameter of sheath. Outlet tube diameter has to be bigger than the inlet diameter. Mechanism to attach to sealing assembly is by screw and thread but it can be anything which is simple to operate and disassemble when needed. The whole piece can be preferably made of brass but it can also be of steel or any other material which can be used in surgical instrument.

Sealing assembly houses a silicon flap valve which opens up when some instrument passes without damaging the instrument and prevents leakage of air and fluid with or without instrument in place. It can be replaced by any other mechanism which is effective and non-traumatic to optics of endoscope.

Ureteric catheter with holes at a distance of one cm in first 10 cm is very useful when one injects air/contrast from below via ureteric catheter, contrast/air fill up whole upper ureter and renal pelvis simultaneously, even in presence of big/stag horn stone. Contrast/air do not have to overflow from one area to other areas of renal pelvis. This makes easy to decide which calyx to puncture and puncture the desired calyx. It is useful to provide retrograde flow of fluid in PCS and stops passage of fragments going down the ureter. As it provides continuous fluid in PCS, during suction the system is never completely collapsed preventing excessive suction on delicate mucosa. It is very essential in operation of percutaneous renal surgery.

The operation of the sheath assembly in such endoscopic surgery and its advantages are discussed hereunder:

When an operation of stone removal is to be done, the sheath assembly of the present advancement can be used as detailed hereunder.

Under anaesthesia, a ureteric catheter with multiple holes in first 10 cm is passed in renal pelvicalyceal system (PCS) from urethra by doing cystoscopy. In prone position, radiographic contrast medium is instilled in PCS to visualize it under fluoroscopy. Suitable calyx is selected for desired route of entry in PCS and is punctured by initial puncture needle. Once entry into suitable calyx is confirmed by free flow of fluid, a guide wire is passed through the needle in the PCS. Retrograde fluid via ureteric catheter is started. Over a guide wire, dilator cum obturator (FIG. 2f) is passed up to PCS. Over dilator, sheath of 10/12 F size (3.66-4 mm diameter) of suitable length (12, 16 or 20 cm) is passed up to PCS. This way dilatation becomes a single step procedure. It prevents bleeding from tract, loss of tract & makes procedure faster and safer. Suction unit (FIG. 2d, 2e) is attached to sheath. Operating endoscope of suitable size is passed via sealing cap (5) into the suction unit to pass thorough tubular sheath (FIG. 2b) to reach the PCS. Entire PCS is visualized. Operating endoscope has channel for flow of normal saline fluid to continuously enter the PCS. Same channel is used for passage of laser fiber (Holmium Yag), biprong forceps or triprong forceps or similar rigid instrument for different action inside PCS. Stone is located and laser energy is applied on stone by touching the stone by laser fiber (200 to 600 micron size). Laser energy is absorbed by stone and stone is broken into small pieces and dust. These dust and fragments disturbs the vision and these have to come out of body.

As described hereinbefore the sheath assembly of the present invention has suction attached to it and it is continuously on. There is small suction controlling opening (10) in reservoir. If the surgeon closes the opening with a finger, suction is applied to tubular sheath and hence inside the PCS. Suction activated during laser lithotripsy sucks all dust and fragments from PCS to inside of sheath (FIG. 2b). Once sucked into tubular sheath (2a/2b/2c), it enters the reservoir (1) and goes out via suction tube (9) to suction machine bottle.

Importantly, the mechanism of reservoir (1) is such that once the fragments have entered the reservoir, they cannot go back in the sheath. Fragments have only one way to go and that is outlet tube.

The construction of reservoir at inlet in form of perpendicular wall and is such that anything that has come at the end of sheath will fall in reservoir and has no chance to go back in the sheath. Outlet tube diameter is more than the inlet diameter. So anything that has come from inlet/sheath will invariably pass through outer tube in the suction bottle. There is no chance of blockage anywhere beyond reservoir. As our operating endoscope is passing via sealing assembly to reservoir to sheath, any blockage in the inlet/sheath is endoscopically visible and can be dealt with under vision. Cylindrical construction of reservoir with outlet tube is preferred such that anything that is present in reservoir will easily enter the outlet especially when there is suction force to suck it.

The suction controlling opening exactly opposite to outlet tube is open to air. When suction is on, there is negative suction in outlet tube. It will suck all fluid and fragments from reservoir preventing spillage outside but will not transmit suction pressure inside the sheath and PCS/body cavity. If operating surgeon wants to have suction pressure inside the sheath and hence inside the body, it is possible to just have to close the opening by a finger. The opening is placed at an ergonomically convenient position. If on the other hand the operating surgeon does not want suction inside the body, the finger is lifted up from the opening allowing it to communicate with air.

Also, whenever there are fragments, the surgeon can take the inner end of sheath near the fragments and suction can be applied to suck all fragments. This way all the fragments from the PCS can be removed under vision. Moreover, in case fragment or stone moves away from endoscope due to fluid from endoscope, suction is activated to bring it back towards endoscope. This way migration of stone and fragments in the distant calyx or ureter is also prevented.

Complete inspection of PCS is done. Once it is confirmed that every possible stone is removed, the sheath is taken out without leaving any nephrostomy tube in the tract. As the tract size is very small, there is minimal chance of bleeding. There is less pain and early recovery.

Figure 3A:
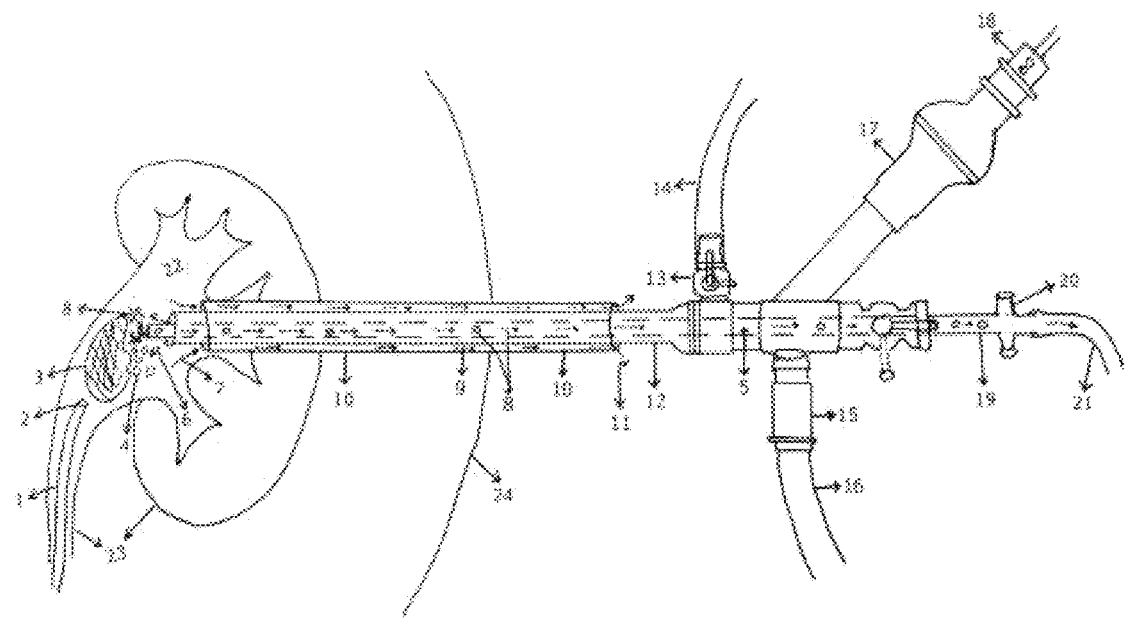

The above discussed advantages in the sheath assembly of the present invention with respect to the conventional sheath would be further apparent from the illustrations of the assembly of the various operating gadgets in relation to the conventional renal sheath and the sheath assembly with suction in accordance with the present invention illustrated by way of accompanying FIGS. 3(a) and 3 (b) (the existing renal sheath) and the accompanying FIG. 4 (the sheath assembly of the present advancement) used for the purposes of endoscopic surgery.

Reference is now invited to accompanying FIG. 3(a) which illustrates the manner of installation and use of the existing renal sheath in endoscopic surgery such as when surgeon wants to remove a stone/stones (3) from upper urinary tract/renal pelvis (22) by percutaneous surgery. As clearly illustrated in said figure, in such operation the surgeon places an open ended ureteric catheter (1) in renal pelvis region (22). After putting patient in prone position, he injects contrast/air in renal pelvis via ureteric catheter from below. As ureteric catheter has only a terminal open end (2), all contrast/air has to go in a particular area of renal pelvis. Contrast overflows from that area to fill other parts of renal pelvis. All parts of renal pelvis are not simultaneously filled or not filled especially in big/staghorn stone. The surgeon then punctures the desired calyx via initial puncture needle. He places a guide wire via puncture needle in the renal pelvis (22). Over a guide wire, serial dilators are passed to dilate the tract to 8 to 10 mm size (24 to 30F). This big tract size is associated with problem of bleeding, adjacent organ injury, possible loss of tract & others. Over the dilator, the existing renal sheath (10) in form of hollow tube of uniform diameter of 8 to 11 mm size is placed extending from skin surface (24) to renal pelvis (22). Via renal sheath, a nephroscope (12) of 6 to 8 mm size is placed in renal pelvis (22) to visualize the stone (3). Fiber optic cable (16) is attached to light pillar (15) of nephroscope (12) to transmit light inside the renal pelvis (22). Endo vision camera (18) is attached to eye piece (17) of nephroscope to transmit images from inside the renal pelvis to outside body on a television monitor. Surgeon operates by seeing in the monitor. Normal saline/irrigation tubing (14) is attached to stop cock (13) of nephroscope to allow normal saline to enter (6) the renal pelvis (22) to keep vision clear in the renal pelvis. There is a straight instrument channel in the nephroscope (12) of 2 to 4 mm size. Various instruments like pneumatic probe, laser fiber, forceps & suction cannula (19) are used. Stone is broken into small pieces (4) by pneumatic probe/laser fiber. Suction cannula (19) is attached to a suction tubing (21) to connect to suction machine. Suction cannula (19) has a trumpet valve (20). Trumpet valve (20) controls suction applied in renal pelvis (22) to suck the fluid & stone fragments (8). Whatever normal saline is going in it has to come out (7) otherwise intra renal pressure will rise. Whatever fluid is going in comes out of renal pelvis (22) by the side of nephroscope (12) via renal sheath (11). All fluid drains out by overflowing (11) as outer end of sheath is open to air alongwith fluid, small stone fragments & dust (4, 9) also coming out via renal sheath. Once stone is completely removed, nephrostomy (a tube from renal pelvis to outside body) is usually kept to control bleeding.

Reference is next invited to yet further illustration of an existing renal sheath based operative gadget and its assembly involved in the operative procedure such as when surgeon wants to remove a stone/stones (3) from upper urinary tract/renal pelvis (23) by percutaneous surgery.

Figure 3B:
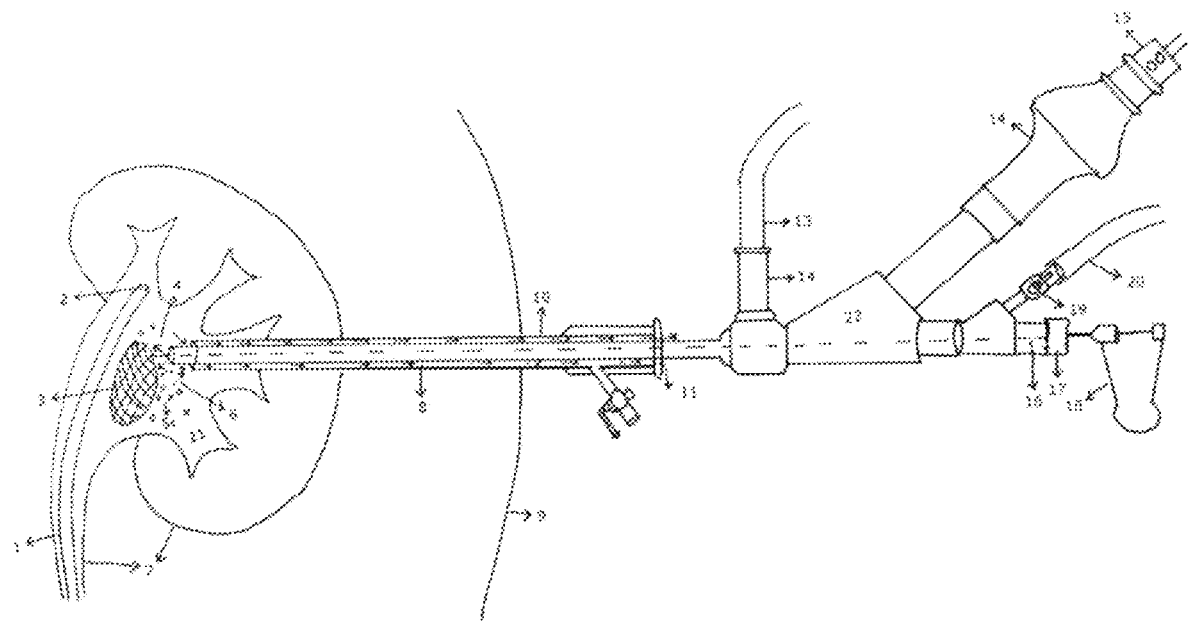

As shown in said FIG. 3b, when surgeon wants to remove a stone/stones (3) from upper ureter or renal pelvis (21) of kidney (7) by percutaneous surgery, he places an open ended ureteric catheter (1) in renal pelvis (21). After putting patient in prone position, the surgeon injects contrast/air in renal pelvis via ureteric catheter from below. As ureteric catheter has only a terminal open end (2), all contrast/air has to go in a particular area of renal pelvis (21). Contrast overflows from that area to fill other parts of renal pelvis. All parts of renal pelvis (21) are not simultaneously filled or not filled especially in big/staghorn stone. He punctures the desired calyx via initial puncture needle. He then places a guide wire via puncture needle in the renal pelvis (21). Over a guide wire, serial dilators are passed to dilate the tract to 5 to 7 mm size (15 to 21F). This big tract size may be associated with problem of bleeding, adjacent organ injury, possible loss of tract & others. Over the dilator, existing renal sheath (10) in form of hollow tube of uniform diameter of 6 to 8 mm size (outer diameter) with outer end bigger in size with stop cock is placed extending from skin surface (9) to renal pelvis (21). Via renal sheath (10), a nephroscope (22) of 4 mm size is placed in renal pelvis to visualize the stone (3). Fiber optic cable (13) is attached to light pillar (12) of nephroscope (22) to transmit light inside the renal pelvis (21). Endo vision camera (15) is attached to eye piece (14) of nephroscope to transmit images from inside the renal pelvis to outside body on a television monitor. Surgeon operates by seeing in the monitor. Normal saline/irrigation tubing (20) is attached to stop cock (19) of nephroscope (22) to allow normal saline to enter (4) the renal pelvis to keep vision clear in the renal pelvis. There is a straight instrument channel (16) of 1.6 mm size (5F) in the nephroscope. Various instruments like pneumatic probe, laser fiber & forceps are used. As the channel size is small, suction cannula cannot be used. Stone is broken into small pieces (5) by pneumatic probe/laser fiber (18). Small fragments and fluid cannot be sucked out from renal pelvis (21) as there is no provision for suction. Whatever normal saline is going in (4) has to come out (6) otherwise intra renal pressure will rise. Whatever fluid is going in comes out (6) of renal pelvis (21) by the side of nephroscope (22) via renal sheath (10) as shown (11). All fluid drains out by overflowing (11) as outer end of sheath is open to air. With fluid, small stone fragments & dust (5) also comes out (8) via renal sheath (11). Once stone is completely removed, nephrostomy (a tube from renal pelvis to outside body) may be kept to control bleeding.

In order to explain further the manner of installation for operative purposes and advantages in the sheath assembly of the present invention in such endoscopic surgery and the like reference is now invited to accompanying FIG. 4 which illustrates the advanced sheath based operative gadgets and its assembly in accordance with the present invention such as may be applied to remove a stone/stones (4) from upper urinary tract/renal pelvis (29) by percutaneous surgery.

Thus, in case of the sheath assembly of the present invention, when surgeon wants to remove a stone/stones (4) from upper ureter or renal pelvis (29) by percutaneous surgery, he places a ureteric catheter (1) with multiple holes in first 10 cms (2) in renal pelvis (29). After putting patient in prone position, he then injects contrast/air in renal pelvis via ureteric catheter from below. As ureteric catheter has multiple opening in first 10 cm (2), contrast/air fill up whole upper ureter and entire renal pelvis (29) simultaneously. Contrast does not overflow from one area to other parts of renal pelvis. All parts of renal pelvis are simultaneously filled even in big/staghorn stone. The surgeon then punctures the desired calyx via initial puncture needle. He places a guide wire via puncture needle in the renal pelvis (29). Over a guide wire, dilator cum obturator, also shown in FIG. 2f, is passed to dilate the tract as a single step to 3 to 3.3 mm size. Such small tract size is advantageously very less likely to be associated with problem of bleeding, adjacent organ injury, possible loss of tract & others. Over the dilator (refer also FIG. 20, tubular sheath (11) in form of hollow tube of uniform diameter of 4 mm size (outer diameter) is placed extending from skin surface (10) to renal pelvis (29). Tubular sheath (also shown in FIGS. 2a, 2b, 2c & 11) is attached to suction unit (of FIG. 2d, 2e) at inlet (30) of reservoir (17). A nephroscope (18) of 2.6 mm size is passed into the renal pelvis (29) via sealing cap (16) to silicon flap valve (15) to reservoir (17) to inlet (30) of reservoir to tubular sheath (11). Suction tube (14) is attached to outlet (13) of reservoir (17). Suction tube (14) is attached to suction machine. Suction machine is always on during the procedure. There is an opening (12) to control the suction power inside the reservoir (17) and in the tubular sheath (11). When the suction control opening (12) is open, it sucks air from outside into the reservoir and whatever fluid and fragments entering into the reservoir (17) is sucked into the outlet (13) of reservoir (17). Outlet diameter is preferably maintained more than the inlet diameter so that there is no possibility of blockage of outlet. Thus whatever enters the reservoir, will always find a way out. There is no suction power in the tubular sheath. When the suction control opening (12) is closed by finger, suction power is present in the renal pelvis (29) and tubular sheath (11). This suction power helps to drain fluid and stone fragments from renal pelvis (29). It lowers the intrapelvic pressure as per wish of surgeon. Fiber optic cable (20) is attached to light pillar (19) of nephroscope (27) to transmit light inside the renal pelvis (29). Endo vision camera (26) is attached to eye piece (25) of nephroscope to transmit images from inside the renal pelvis to outside body on a television monitor. Surgeon operates by seeing in the monitor. Normal saline/irrigation tubing (22) is attached to stop cock (21) of nephroscope (18) to allow normal saline (28) to enter through (6) the renal pelvis (29) to keep vision clear in the renal pelvis. There is a straight instrument channel (23) in the nephroscope of 1 mm size (3F). Various instruments like pneumatic probe, laser fiber & forceps etc. (24) are used. Stone (4) is broken into small pieces (5) by pneumatic probe/laser fiber (24). Small fragments and fluid can be sucked out through (7) from renal pelvis (29) by closing the suction control opening (12) with the finger. Whatever normal saline is going in (6) has to come out (7) otherwise intra renal pressure will rise. Whatever fluid is going in comes out (7) of renal pelvis (29) by the side of nephroscope via tubular sheath (8). All fluid drains out by overflowing in the reservoir (17). With fluid, small stone fragments & dust (5) also comes out via (8) tubular sheath. The construction of the reservoir is such that whatever enters in reservoir cannot go back in the tubular sheath (11) & renal pelvis (29). There is continuous suction in the reservoir to suck out whatever has come in via outlet of reservoir to suction tube to suction machine. If the fragment is big or surgeon want to have a bigger channel to suck, endoscope is withdrawn gradually while suction control opening (12) is closed by finger. Suction channel is now 3.3 mm in size & the surgeon actually can see what is being sucked out. There is continuous flow of normal saline entering the renal pelvis via ureteric catheter (1). The flow of saline helps the fragments to move toward the sheath and will not allow the mucosa to be sucked. Once stone is completely removed, there is no need to keep the nephrostomy (a tube from renal pelvis to outside body). The recovery is very good due to small tract size.

Importantly, it would be clearly apparent from the above illustrations that the construction of the sheath assembly suitable for endoscopic surgery in accordance with the present advancement involving the reservoir and the suction control opening located at reservoir advantageously divide the sheath assembly/unit into two distinctly separable communication zones and the opening decides whether suction communication zones should be limited to the reservoir or extend to the cannula and reservoir both. This is unique and benefits a lot both for the suction from the cannula and also from the reservoir alone and has contributes immensely towards providing the operating surgeon with a user friendly and operation friendly system to clear up the particles and fluid from the operation site as well as from the operating pathway/device.

Moreover, the construction of the sheath assembly has enabled the following advantages:
i) Percutaneous renal surgery is possible with tract size of 10 F (3F=1 mm), needing no dilatation of tract.
ii) There is complete visualization of system due to multihole ureteric catheter. It makes renal puncture easy.
iii) It is possible to use operating endoscope with straight working channel.
iv) There is low intra renal pressure leading to enhanced safety in infected and non-infected cases.
v) There is effective suction on demand similar to ultrasonic lithotripsy, pneumatic lithotripsy or laserclast. But they are not possible in this small size tract in prior art. There is suction available even without lithotripsy.
vi) It is possible to achieve near complete clearance of stone on operation table.
vii) It is safe and efficacious even in hydronephrotic and infected system.
viii) It is useful in wide varieties of cases of urolithiasis and other upper tract diseases.
ix) It requires minimal armamentarium.
x) Simplicity of procedure.
xi) Minimal intraoperative and post-operative complications.
xii) It leads to early discharge and faster recovery and enhanced saving of human hours.

Further the advancement in accordance with another aspect of the present invention residing in the multiple holes based ureteric catheter and its advantageous use in endoscopic surgery such as is discussed hereunder in relation to the accompanying Figures.

For the purpose reference is first invited to accompanying FIG. 5 which illustrates what usually happens normally as far as flow of fluid & pressure kinetics in renal pelvis is concerned.

As shown in said figure, urine produced by kidney comes in renal pelvis (4) from multiple calyces (1) like streams of water (2) forming a river (3). Urine enters ureter (6) via ureteropelvic junction (5) due to rise in pressure in renal pelvis due to continuous entry of urine from calyces. Urine is carried down by wave of peristalsis from renal pelvis (4) to ureter (6) to urinary bladder (7). With urine, small stone and crystals also go down the ureter & then in the urinary bladder in normal individual. If a stone blocks the lumen of ureter (6), person develops pain of stone disease.

Turning now again to FIG. 3a, the same illustrates what is usually done in conventional percutaneous renal surgery.

During Operation of percutaneous renal surgery, there is continuous entry of normal saline (6) via nephroscope but at a very high rate. Presence of renal sheath (10) creates an alternative path (7-9-11) for flow of fluid to outside of body in addition to path across ureter down as is naturally happening (shown in FIG. 5). This path (7-9-11), being very wide, does not allow the renal pressure to rise and minimal fluid and fragments (4) go down the ureter. To keep this path as big as possible, telescope (12) has to be smaller or tract has to be bigger with its own disadvantages. Use of suction helps to suck out (8) all small fragments (4) from renal pelvis. So during surgery, surgeon has to repeatedly stop the breaking of stone to suck out fragments or use inbuilt suction with lithotripsy as in ultrasonic lithotripsy or pneumatic lithotripsy with suction. Such systems need larger instrument channel with its own problem of increasing the tract size. If the fragment/fragments (4) going down the ureter with the downward flow (3 of FIG. 5) are more, it may block the ureter & person may develop the stone pain after surgery of percutaneous renal surgeryand many time leakage of urine from the tract site (24). Surgeon puts a stent extending from renal pelvis (22) down the ureter (23) to urinary bladder (7 of FIG. 5) to avoid this problem with its own complications. Surgeon may put a nephrostomy tube extending from renal pelvis (22) to skin surface (24) across the tract with its own problems. In short there is problem of fragments going down the ureter with possibility of blockage of ureter. To solve this problem, additional problems are created.

FIG. 3b is again an illustration of what happens in smaller tract size.

During operation of percutaneous renal surgery, there is continuous entry of normal saline (4) but at much higher rate. Presence of sheath (10) creates an alternative path (6-8-11) for flow of fluid to outside body in addition to path across ureter down as is naturally happening (shown as 3 in FIG. 5). This path (6-8-11) does not allow the renal pressure to rise and minimal fluid and fragments (5) go down the ureter. To keep this path (8) as big as possible, telescope (22) has to be smaller or tract has to be bigger with its own disadvantages. Due to small size telescope, suction mechanism alone & ultrasonic lithotripsy & pneumatic lithotripsy with suction are not possible. There are high chances of fragments going down the ureter especially if the stone is near junction of ureter & pelvis (5 of FIG. 5) or in the ureter (7). If flow of normal saline from nephroscope (4) is towards ureter due to angulation of nephroscope, it is very easy for stone fragments (5) to go down ureter and fly away from nephroscope. If the stone fragments have gone the ureter, it may block the ureter & person may develop stone pain even after surgery of percutaneous renal surgeryand many times leakage of urine from the tract site (9). Pain and leakage subside only after the fragments have spontaneously passed from ureter (6 of FIG. 5) to bladder (7 of FIG. 5). If they do not pass spontaneously, another operative procedure is required to remove those fragments with added risk, agony and loss of money and man power. Alternatively surgeon puts a stent or nephrostomy with its own disadvantages.

Reference is now invited to accompanying FIG. 6 which shows an open ended multihole ureteric catheter in accordance with the present invention.

As shown in FIG. 6, the ureteric catheter has a terminal open end (1) with markers (3) at equidistance to know how much catheter is inserted. It is radiopaque and other open end (5) with a uniform inner diameter to allow fluid to go in & come out.

The extra feature added is multiple holes (2) in first few centimetres of ureteric catheter (4).

Ureteric catheter is placed in such a way that few holes are in ureter & few are in renal pelvis. When fluid is allowed to go from outer end (5) of ureteric catheter, this arrangement of hole ensures free flow of saline from ureter to renal pelvis in all areas of pelvis where there is hole.

Reference is now again invited to accompanying FIG. 4 to demonstrate the advantages residing in the involvement of the sheath assembly along with the multi hole ureteric catheter in accordance with the present advancement.

As would be clearly apparent from FIG. 4, during operation of percutaneous renal surgery, there is continuous/intermittent flow (6) from nephroscope regulated by stopcock (21). Additionally by way of the involvement of the mutihole catheter in accordance with the present invention it is possible to achieve continuous flow (3) of normal saline from multihole ureteric catheter (1). Multiple holes, some in ureter &some in renal pelvis ensures flow from ureter & renal pelvis towards the inner end of sheath as demonstrated (7,8) all the time during the operation of percutaneous renal surgery. This feature of the multihole catheter in accordance with the present invention has four advantages not previously available as follows:

(1) As fluid is coming out from multiple holes instead of single terminal hole, whole renal pelvis and ureter is simultaneously filled. It has advantages when renal pelvis is full of stone. In prior art, whole system cannot be filled simultaneously.

(2) The possible retrograde flow improves vision in renal pelvis as it provides extra flow in renal pelvis (not present in prior art). This is very important as the channel (23) size of nephroscope is small; amount of fluid entering via (6) may be limited especially in presence of instrument (24) in the channel (23). Retrograde flow of saline also permits us to stop the flow (6) if required especially when dealing with stone near ureteropelvic junction & in ureter without losing the vision.

(3) Such retrograde flow achieved for the first time by way of the multihole catheter of the invention changes the pressure flow kinetics of renal pelvis in the procedure with advantages. Changed flow &pressure dynamics (flow from ureter to renal pelvis to outside via sheath) do not allow any fragments & fluid going down the ureter to bladder & keep vision in renal pelvis clear all the time. When surgeon notices high pressure in renal pelvis by distended renal pelvis, he starts active suction by closing suction control opening. This feature augments this unique flow pattern from ureter to renal pelvis to outside. Two features namely retrograde flow from ureter & active suction have synergistic effect. When no fragments have gone down the ureter, there is no need of putting stent & nephrostomy at the end of procedure. Post-operative period is smooth & predictable.

(4) When surgeon activates the suction especially when scope is not in the sheath for bigger fragments to come out, surgeon is not able to see what is happening at inner end of sheath. Continuous flow from ureter pushes stone to come out and augments the suction effect. It also ensures that renal pelvic mucosa is not sucked because there is always some fluid being sucked. It prevents injury to mucosa by suction.

Multiple holes in ureteric catheter in first few centimetres is all what is needed. The placement of ureteric catheter should be such that few holes should be in ureter & few in renal pelvis.

Experimental trials conducted involving the sheath assembly and the multi hole catheter of the present invention in various endoscopic surgery have shown beneficial results and easy of operation and comfort for removal of kidney stone, calyceal stone, multiple stones, upper ureteric stone etc. with excellent result with faster recovery and minimal complications.

Thus, the advancement of the invention is aimed for redefining the way surgeons treat kidney stones and carry out other endoscopic surgery where irrigation of fluid is required. It provides easy removal of return fluid under our control and help to control the body cavity fluid& pressure dynamics. It shifts the suction mechanism from operating surgeon holding endoscope to assistant holding the sheath. It immeasurably improves the comforts of operating surgeon. It allows us to use smaller tract size to operate in closed body cavity. It makes procedure of endoscopy much safer, faster and effective.

I claim:

1. A sheath assembly for different fields of endoscopic surgery involving suction, irrigation and material removal comprising:
   a tubular sheath including a sheath cannula having an inner open end adapted for introducing into a body region requiring surgery and an outer other open end; and
   a suction unit with controllable suction provision operatively connected to said outer other open end of said tubular sheath; comprising a reservoir having;
   a reservoir inlet having a central axis parallel to a reservoir central axis, and operatively connected in line with the outer other open end of the tubular sheath;
   a reservoir outlet operatively connected to a suction machine for facilitating continuous suction from the reservoir, and said reservoir outlet oriented at an angle of 90°+/−15° relative to the reservoir central axis, and said reservoir outlet facing downwards to enable contents from said body region traveling through the outer other open end of the tubular sheath to fall into the reservoir, the contents are prevented from going back into the tubular sheath;
   a releasably attachable sealing assembly, secured to a proximal open end of the reservoir, the releasably attachable sealing assembly when attached forming a proximal end of the reservoir, and operatively connected in line with said reservoir inlet;
   the releasably attachable sealing assembly allows passage of the operating endoscope into the reservoir, and enables assembly of the reservoir and the operating endoscope, the releasably attachable sealing assembly forms a water and air tight seal enabling function of the suction unit; and a suction control opening disposed in operative connection with said reservoir outlet, and the suction control opening disposed on said reservoir;
   wherein when the suction control opening is open it allows air to enter the reservoir of the sheath assembly, and when the suction control opening is closed it does not allow air to enter reservoir of the sheath assembly;
   wherein selective opening and closing of said suction control opening provides alternative suction zones in the sheath assembly and suction of contents from the alternative suction zones during continuous suction, wherein the alternative suction zones are selected from (i) the reservoir and (ii) the tubular sheath, the body region in which the tubular sheath is placed, and the reservoir; the alternative suction zones thereby facilitate suction pressure to alternative suction zone (i) when the suction control opening is open and alternative suction zone (ii) when the suction control opening is closed.

2. The sheath assembly as claimed in claim 1, wherein the suction control opening is disposed on an opposite side of the reservoir relative to the reservoir outlet.

3. The sheath assembly as claimed in claim 1, wherein reservoir outlet is provided facing downwards, to facilitate gravity assisted release of the contents from the reservoir inlet into the reservoir.

4. The sheath assembly as claimed in claim 1, wherein the sealing assembly comprises
   a sealing flap disposed in line with the reservoir inlet which is in turn in line with the tubular sheath passage; and
   a sealing cap on an outside of the sealing flap;
   said sealing assembly allows releasable passage of the operating endoscope into the tubular sheath cannula through the reservoir inlet, and into the said body region requiring surgery and such that the endoscope can be taken out for creating space for suction of fragments and reintroduced without losing tract.

5. The sheath assembly as claimed in claim 1, wherein the reservoir inlet is disposed in a distal wall of the reservoir, the distal wall is perpendicular to the central axis of the reservoir and enables collection of the contents from the reservoir inlet and the suction passage, the distal wall prevents the contents from going back into said body region requiring surgery.

6. The sheath assembly as claimed in claim 1, wherein a diameter of the reservoir inlet is smaller than a diameter of the reservoir outlet, ensuring the contents which are released into the reservoir can be suctioned out through reservoir outlet, the contents are suction out with gravitational assistance by positioning said reservoir outlet facing downwards.

7. The sheath assembly as claimed in claim 1 which is a renal sheath assembly for percutaneous renal surgery.

8. The sheath assembly as claimed in claim 1, wherein a diameter of the tubular sheath allows passage of a dilator cum obturator, the dilator cum obturator comprising one end tapered for a distance of 4 mm to 8 mm and an inside diameter allows passage of a guide wire.

9. A method for carrying out endoscopic surgery involving suction, irrigation and material removal involving the sheath assembly as claimed in claim 4 comprising:
   (i) assembling the sheath assembly by connecting the tubular sheath to suction unit having said sealing assembly;
   (ii) connecting the reservoir outlet to suction machine;
   (iii) placing the tubular sheath in said body region requiring surgery and passing operating endoscope into said tubular sheath via said sealing cap through the sealing flap through the reservoir through the inlet and into in said body region requiring surgery,
   such that the said endoscope can be taken out and reintroduced without losing tract;
   (iv) carrying out the endoscopic surgery involving said sheath assembly maintaining the suction machine on during the process and selectively keeping the suction controlling opening (a) open when no suction effect is desired to alternative suction zone (ii), and fluid and particles are allowed to drain out by overflowing from said body region requiring surgery and (b) closed when the suction is desired to alternative suction zone (ii) to allow the operative fragments and the contents to be sucked out of said body region requiring surgery.

10. The method as claimed in claim 9, wherein the endoscope is taken out from the sheath gradually to provide space in the sheath for larger operative fragments to to drain out and/or be suctioned out.

11. The method as claimed in claim 9, wherein the fluid and/or fragments that are drained out and/or suctioned out are collected in the reservoir, and then drained out of the reservoir.

* * * * *